US008017328B2

(12) United States Patent
Ach et al.

(10) Patent No.: US 8,017,328 B2
(45) Date of Patent: Sep. 13, 2011

(54) GENOME PARTITIONING USING A NICKING ENDONUCLEASE

(75) Inventors: Robert A. Ach, San Francisco, CA (US); Brian J. Peter, Los Altos, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 35 days.

(21) Appl. No.: 12/276,041

(22) Filed: Nov. 21, 2008

(65) Prior Publication Data

US 2010/0129879 A1 May 27, 2010

(51) Int. Cl.
*C12Q 1/68* (2006.01)
*C07H 21/02* (2006.01)
*C07H 21/04* (2006.01)

(52) U.S. Cl. ............................ 435/6; 536/23.1; 536/24.3

(58) Field of Classification Search ..... 435/6; 536/23.1, 536/24.3
See application file for complete search history.

(56) References Cited

U.S. PATENT DOCUMENTS

| | | | | |
|---|---|---|---|---|
| 4,321,365 | A * | 3/1982 | Wu et al. ................... | 536/24.2 |
| 6,660,475 | B2 * | 12/2003 | Jack et al. ................ | 435/6 |
| 6,846,644 | B2 * | 1/2005 | Davis et al. .............. | 435/15 |
| 6,958,217 | B2 * | 10/2005 | Pedersen .................. | 435/6 |
| 2002/0119448 | A1 * | 8/2002 | Sorge et al. .............. | 435/6 |
| 2004/0009507 | A1 * | 1/2004 | Winter et al. ............. | 435/6 |
| 2006/0046251 | A1 * | 3/2006 | Sampson et al. ......... | 435/6 |
| 2008/0286793 | A1 * | 11/2008 | Nagaoka .................. | 435/6 |
| 2009/0068652 | A1 * | 3/2009 | Taylor et al. ............. | 435/6 |

FOREIGN PATENT DOCUMENTS

| | | | |
|---|---|---|---|
| EP | 1176204 | * | 4/2002 |
| WO | WO94/21820 | * | 10/1994 |
| WO | WO 03/087301 | * | 10/2003 |
| WO | WO 2006/012593 | * | 2/2006 |
| WO | WO2007/063807 | * | 7/2007 |

OTHER PUBLICATIONS

Stratagene Catalog, p. 39, 1988.*
New England Biolabs 3 pages showing reconition sequence for EcoRI, BamHI and HindIII (2010).*
Guilfoyle et al., Ligation-mediated PCR amplification of specific fragments from a Class-II restricrtion endonuclease total digest. Nucleic Acids Research 25 (9) :1854-1858 (1997).*
Nicking Endonuclease from New England Biolabs (2006).*
Kiesling et al., Sequence specific detection of DNA using nicking endonuclease signal amplification (NESA). Nucleic Acids Research 35(18) : e117 pp. 1-9 (Sep. 2007).*
Hosoda et al., A novel sequence-specific RNA quantification method using nicking endonuclease, dual-labeled fluorescent DNA probe, and conformation-interchangeable oligo-DNA. RNA 14 : 584-592 (2008).*
Saiki et al.Genetic analysis of amplified DNA with immobilized sequence-specific oligonucleotide probes PNAS 86(16) : 6230-6234 (1989).*
Whisenant et al., Evolution and sequence analysis of a human Y-chromosomal DNA fragment. Journal of Molecular Evolution 33(2) : 133-141 (1991).*
Nt.Alwl product description downloaded from the New England Biolabs website.*
NbBsml product description downloaded from the New England Biolabs website.*
Kuhn, H., et al. Labeling of unique sequences in double-stranded DNA at sites of vicinal nicks generated by nicking endonucleases. Nucleic Acids Research. 2008, vol. 36, No. 7, pp. e40.

* cited by examiner

*Primary Examiner* — E C Whisenant
(74) *Attorney, Agent, or Firm* — James S. Keddie; Bret E. Field; Bozicevic, Field & Francis (57) ABSTRACT

A method for partitioning a genome is provided. In certain embodiments, the method comprises: a) nicking a region of the genome using a sequence-specific nicking endonuclease to produce a nicked double-stranded genomic region; b) hybridizing the nicked double-stranded genomic region with an oligonucleotide comprising: i. an affinity tag; and ii. a nucleotide sequence that is complementary to the nucleotide sequence that is immediately adjacent to the nick site, to produce a duplex in which a terminal nucleotide of the oligonucleotide lies immediately adjacent to said a nucleotide of the nick site; c) ligating the terminal nucleotide of the oligonucleotide to the nucleotide of the nick site to produce a ligation product; and d) separating the ligation product from unligated products using the affinity tag. Compositions and kits for practicing the method are provided.

20 Claims, 8 Drawing Sheets

GENOME PARTITIONING USING A NICKING ENDONUCLEASE

BACKGROUND

Methods for genome partitioning, i.e., the separation of selected regions of a genome from other regions, find use in a variety of genomic analysis applications, including, but not limited to SNP analysis, sequencing, mutation detection and the detection of chromosomal rearrangements. This disclosure relates, in part, to a method for genome partitioning.

SUMMARY

A method for partitioning a genome is provided. In certain embodiments, the method comprises: a) nicking a region of the genome using a sequence-specific nicking endonuclease to produce a nicked double-stranded genomic region; b) hybridizing the nicked double-stranded genomic region with an oligonucleotide comprising: i. an affinity tag; and ii. a nucleotide sequence that is complementary to the nucleotide sequence that is immediately adjacent to the nick site, to produce a duplex in which a terminal nucleotide of the oligonucleotide lies immediately adjacent to said a nucleotide of the nick site; c) ligating the terminal nucleotide of the oligonucleotide to the nucleotide of the nick site to produce a ligation product; and d) separating the ligation product from unligated products using the affinity tag. Compositions and kits for practicing the method are provided.

BRIEF DESCRIPTION OF THE FIGURES

FIGS. 2A-2C schematically illustrates exemplary methods for isolating a genomic region.

DEFINITIONS

The term "sample" as used herein relates to a material or mixture of materials, typically, although not necessarily, in liquid form, containing one or more analytes of interest.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively).

The term "nucleic acid sample," as used herein denotes a sample containing nucleic acids.

The term "target polynucleotide," as use herein, refers to a polynucleotide of interest under study. In certain embodiments, a target polynucleotide contains one or more sequences that are of interest and under study.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 10 to 50 nucleotides in length. Oligonucleotides may contain ribonucleotide monomers (i.e., may be oligoribonucleotides) or deoxyribonucleotide monomers. An oligonucleotide may be 10 to 20, 11 to 30, 31 to 40, 41 to 50, 51-60, 61 to 70, 71 to 80, 80 to 100, 100 to 150 or 150 to 200 nucleotides in length, for example.

The term "duplex," or "duplexed," as used herein, describes two complementary polynucleotides that are base-paired, i.e., hybridized together.

The term "amplifying" as used herein refers to generating one or more copies of a target nucleic acid, using the target nucleic acid as a template.

An "array," includes any two-dimensional or substantially two-dimensional (as well as a three-dimensional) arrangement of spatially or optically addressable regions bearing nucleic acids, particularly oligonucleotides or synthetic mimetics thereof, and the like. Where the arrays are arrays of nucleic acids, the nucleic acids may be adsorbed, physisorbed, chemisorbed, or covalently attached to the arrays at any point or points along the nucleic acid chain.

Any given substrate may carry one, two, four, eight or more arrays disposed on a surface of the substrate. Depending upon the use, any or all of the arrays may be the same or different from one another and each may contain multiple spots or features. An array may contain one or more, including more than two, more than ten, more than one hundred, more than one thousand, more ten thousand features, or even more than one hundred thousand features, in an area of less than 20 $cm^2$ or even less than 10 $cm^2$, e.g., less than about 5 $cm^2$, including less than about 1 $cm^2$, less than about 1 $mm^2$, e.g., 100 $\mu m^2$, or even smaller. For example, features may have widths (that is, diameter, for a round spot) in the range from a 10 $\mu m$ to 1.0 cm. In other embodiments each feature may have a width in the range of 1.0 $\mu m$ to 1.0 mm, usually 5.0 $\mu m$ to 500 $\mu m$, and more usually 10 $\mu m$ to 200 $\mu m$. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, 20%, 50%, 95%, 99% or 100% of the total number of features). Inter-feature areas will typically (but not essentially) be present which do not carry any nucleic acids (or other biopolymer or chemical moiety of a type of which the features are composed). Such inter-feature areas typically will be present where the arrays are formed by processes involving drop deposition of reagents but may not be present when, for example, photolithographic array fabrication processes are used. It will be appreciated though, that the inter-feature areas, when present, could be of various sizes and configurations.

Each array may cover an area of less than 200 cm$^2$, or even less than 50 cm$^2$, 5 cm$^2$, 1 cm$^2$, 0.5 cm$^2$, or 0.1 cm$^2$. In certain embodiments, the substrate carrying the one or more arrays will be shaped generally as a rectangular solid (although other shapes are possible), having a length of more than 4 mm and less than 150 mm, usually more than 4 mm and less than 80 mm, more usually less than 20 mm; a width of more than 4 mm and less than 150 mm, usually less than 80 mm and more usually less than 20 mm; and a thickness of more than 0.01 mm and less than 5.0 mm, usually more than 0.1 mm and less than 2 mm and more usually more than 0.2 mm and less than 1.5 mm, such as more than about 0.8 mm and less than about 1.2 mm.

Arrays can be fabricated using drop deposition from pulse-jets of either precursor units (such as nucleotide or amino acid monomers) in the case of in situ fabrication, or the previously obtained nucleic acid. Such methods are described in detail in, for example, the previously cited references including U.S. Pat. Nos. 6,242,266, 6,232,072, 6,180,351, 6,171,797, 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used. Inter-feature areas need not be present particularly when the arrays are made by photolithographic methods as described in those patents.

An array is "addressable" when it has multiple regions of different moieties (e.g., different oligonucleotide sequences) such that a region (i.e., a "feature" or "spot" of the array) at a particular predetermined location (i.e., an "address") on the array contains a particular sequence. Array features are typically, but need not be, separated by intervening spaces. An array may be spatially or optically addressable, for example.

The terms "determining", "measuring", "evaluating", "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

As used herein, the term "$T_m$" refers to the melting temperature of an oligonucleotide duplex at which half of the duplexes remain hybridized and half of the duplexes dissociate into single strands. The $T_m$ of an oligonucleotide duplex may be experimentally determined or predicted using the following formula $T_m=81.5+16.6(\log_{10}[Na^+])+0.41$ (fraction G+C)−(60/N), where N is the chain length and [Na$^+$] is less than 1 M. See Sambrook and Russell (2001; Molecular Cloning: A Laboratory Manual, 3$^{rd}$ ed., Cold Spring Harbor Press, Cold Spring Harbor N.Y., ch. 10). Other formulas for predicting $T_m$ of oligonucleotide duplexes exist and one formula may be more or less appropriate for a given condition or set of conditions.

As used herein, the term "$T_m$-matched" refers to a plurality of nucleic acid duplexes having $T_m$s that are within a defined range.

As used herein, the term "single nucleotide polymorphism", or "SNP" for short, refers to single nucleotide position in a genomic sequence for which two or more alternative alleles are present at appreciable frequency (e.g., at least 1%) in a population.

The term "free in solution," as used here, describes a molecule, such as a polynucleotide, that is not bound or tethered to another molecule.

The term "denaturing," as used herein, refers to the separation of a nucleic acid duplex into two single strands.

The term "partitioning", with respect to a genome, refers to the separation of one part of the genome from the remainder of the genome to produce a product that is isolated from the remainder of the genome. The term "partitioning" encompasses enriching.

The term "genomic region", as used herein, refers to a region of a genome, e.g., an animal or plant genome such as the genome of a human, monkey, rat, fish or insect or plant. In certain cases, an oligonucleotide used in the method described herein may be designed using a reference genomic region, i.e., a genomic region of known nucleotide sequence, e.g., a chromosomal region whose sequence is deposited at NCBI's Genbank database or other database, for example. Such an oligonucleotide may be employed in an assay that uses a sample containing a test genome, where the test genome contains a cleaving site for a nicking endonuclease adjacent to a binding site for the oligonucleotide. The precise nucleotide sequence that flanks the oligonucleotide binding site in a test genome may known or unknown.

The term "nicking", as used herein, refers to a reaction that breaks the phosphodiester bond between two nucleotides in one strand of a double-stranded DNA molecule to produce a 3'-hydroxyl group and a 5' phosphate group.

The term "nick site", as used herein, refers to the site at which a double-stranded DNA molecule has been nicked.

The term "nicked double-stranded genomic region", as used herein, refers to a double-stranded DNA molecule that contains a nick site.

The term "sequence-specific nicking restriction endonuclease" refers to an enzyme that nicks double-stranded DNA at a specific sequence to which the enzyme binds. Such an enzyme does not induce a double-stranded break at its binding site. Rather, a sequence-specific nicking restriction endonuclease catalyzes breakage of a phosphodiester bond in only one strand of a double-stranded DNA molecule.

The term "affinity tag", as used herein, refers to moiety that can be used to separate a molecule to which the affinity tag is attached from other molecules that do not contain the affinity tag. In certain cases, an "affinity tag" may bind to the "capture agent", where the affinity tag specifically binds to the capture agent, thereby facilitating the separation of the molecule to which the affinity tag is attached from other molecules that do not contain the affinity tag.

With reference to two nucleic acid molecules or two nucleotides (i.e., a first oligonucleotide and a second oligonucleotide), the term "immediately adjacent", as used herein, refers to next to each other with no intervening nucleotides. Two adjacent nucleotides in a nicked double-stranded DNA molecule lie on either side of the nick site of that molecule.

The term "terminal nucleotide", as used herein, refers to the nucleotide at either the 5' or the 3' end of a nucleic acid molecule. The nucleic acid molecule may be in double-stranded (i.e., duplexed) or in single-stranded form.

The term "ligating", as used herein, refers to the enzymatically catalyzed joining of the terminal nucleotide at the 5' end of a first DNA molecule to the terminal nucleotide at the 3' end of a second DNA molecule.

The term "strand displacement", as used herein, refers to the replacement of one strand of a double-stranded nucleic acid molecule with another single-stranded nucleic acid molecule (e.g., an oligonucleotide) that base pairs to the same site as the strand that is removed. When strand displacement occurs between two nick sites, the sequence of nucleotides between the nick sites is replaced with an oligonucleotide that base pairs to a sequence that is complementary to the sequence that is replaced.

DESCRIPTION OF EXEMPLARY EMBODIMENTS

A method for partitioning a genome is provided. In certain embodiments, the method comprises: a) nicking a region of the genome using a sequence-specific nicking endonuclease to produce a nicked double-stranded genomic region; b) hybridizing the nicked double-stranded genomic region with an oligonucleotide comprising: i. an affinity tag; and ii. a nucleotide sequence that is complementary to the nucleotide sequence that is immediately adjacent to the nick site, to produce a duplex in which a terminal nucleotide of the oligonucleotide lies immediately adjacent to said a nucleotide of the nick site; c) ligating the terminal nucleotide of the oligonucleotide to the nucleotide of the nick site to produce a ligation product; and d) separating the ligation product from unligated products using the affinity tag. Compositions and kits for practicing the method are provided.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Method for Genome Partitioning

As noted above, a method for partitioning a genome is provided. In general terms, the first step in the method includes contacting a sample containing a test genome with a so-called nicking endonuclease (or "NEase)" under conditions suitable for activity of the nicking endonuclease to nick a region of the genome, thereby producing a nicked double-stranded genome region. The nick site is flanked by a first nucleotide and a second nucleotide that are immediately adjacent to one another (i.e., not separated by any intervening nucleotides). In certain cases (depending on how the method is practiced), the genome may be contacted with a plurality (i.e., two or more, e.g., two, three, four or five) of different nicking endonucleases to produce a plurality of different nick sites. In certain embodiments, if a plurality of nicking endonucleases are used, the nicking endonucleases may be selected so as to nick at defined sites in only one DNA strand of a double-stranded region, such that the nick sites are distanced by from 15 to 500 nucleotides (e.g., in the range of 18 to 200 nucleotides or in the range of 25 to 150 nucleotides), although distances outside of this ranges are envisioned, to produce double nicked double-stranded region containing two or more nick sites.

In general terms, a particular nicking endonuclease or combination thereof may be chosen because it has a target site that is proximal to (i.e., within 100 kb of, e.g., within 50 kb of, within 10 kb of, within 5 kb of, within, 1 kb of or within 500 bases of) a genomic region of interest, e.g., a region under investigation such as a region of unknown sequence, or a region containing a SNP, nucleotide insertion, nucleotide deletion, rearrangement, etc. Depending on the desired site, a variety of nicking endonucleases may be employed in the subject method, including, but not limited to: Nb.BsmI, Nb.BbvCI, Nb.BsrDI, Nb.BtsI, Nt.BbvCI, Nt.AlwI and Nt.B-stNBI (Bellamy et al. J. Mol. Biol. 2005 345, 641-653; Heiter et al J. Mol. Biol. 2005 348, 631-640; Xu. et al Proc. Natl. Acad. Sci. USA 2001 98, 12990-12995; Samuelson et al Nucl. Acids Res. 2004 32, 3661-3671; Zhu et al. J. Mol. Biol. 2004 337, 573-583; Morgan. et al. Biol. Chem. 2000 381, 1123-1125; Chan Nucl. Acids Res. 2004 32, 6187-6199 and Sasnauskas Proc. Natl. Acad. Sci. USA 2003 100, 6410-6415) as well as nicking enzymes that have been engineered from TypeIIs restriction enzymes (e.g., variants of AlwI, Bpu10I, BbvCI, BsaI, BsmBI, BsmAI, BsmI, BspQI, MlyI, Mva1269I and SapI, etc.) Conditions for the use of those enzymes are known and may be supplied with manufacturer's instructions when purchased.

Figure 1:
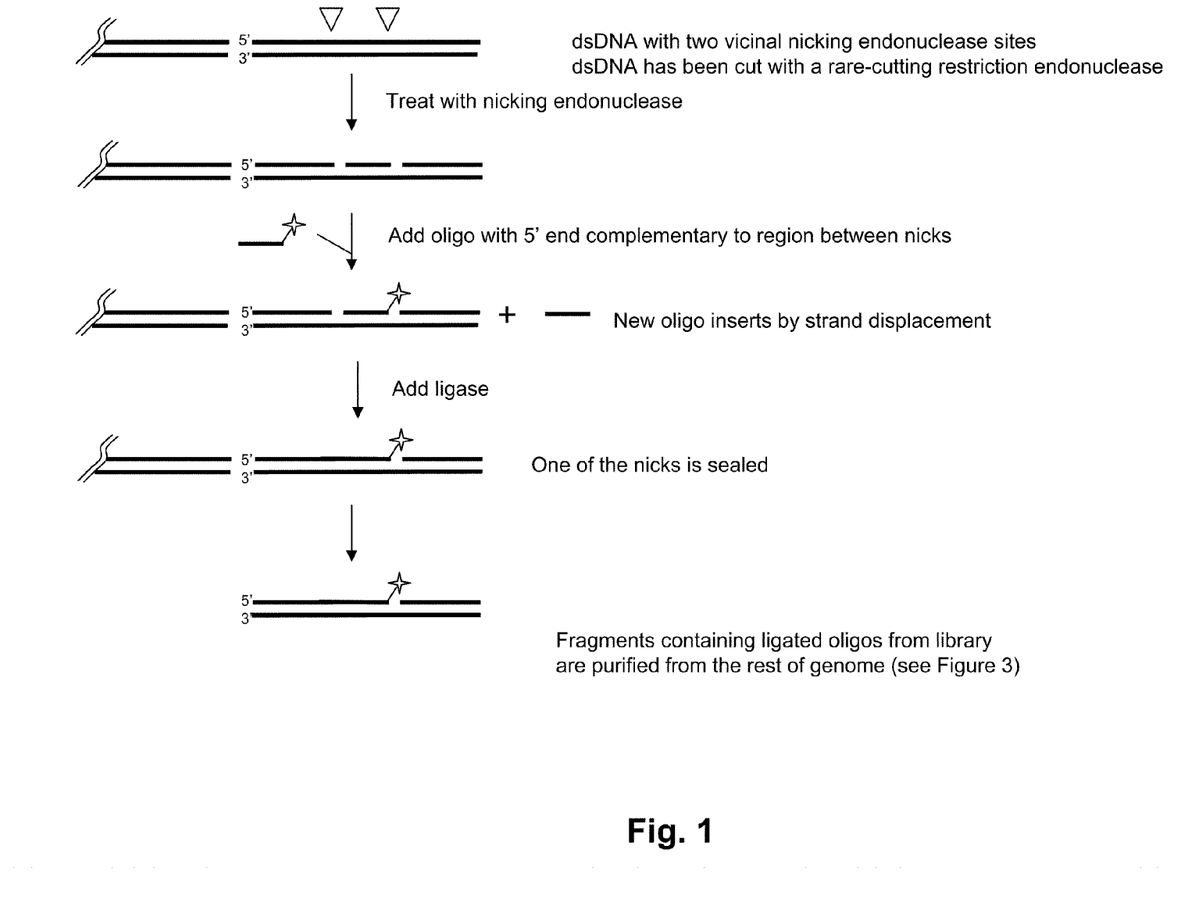
FIG. 1 schematically illustrates a first embodiment of a genome partitioning method described in greater detail below.
Figure 4:
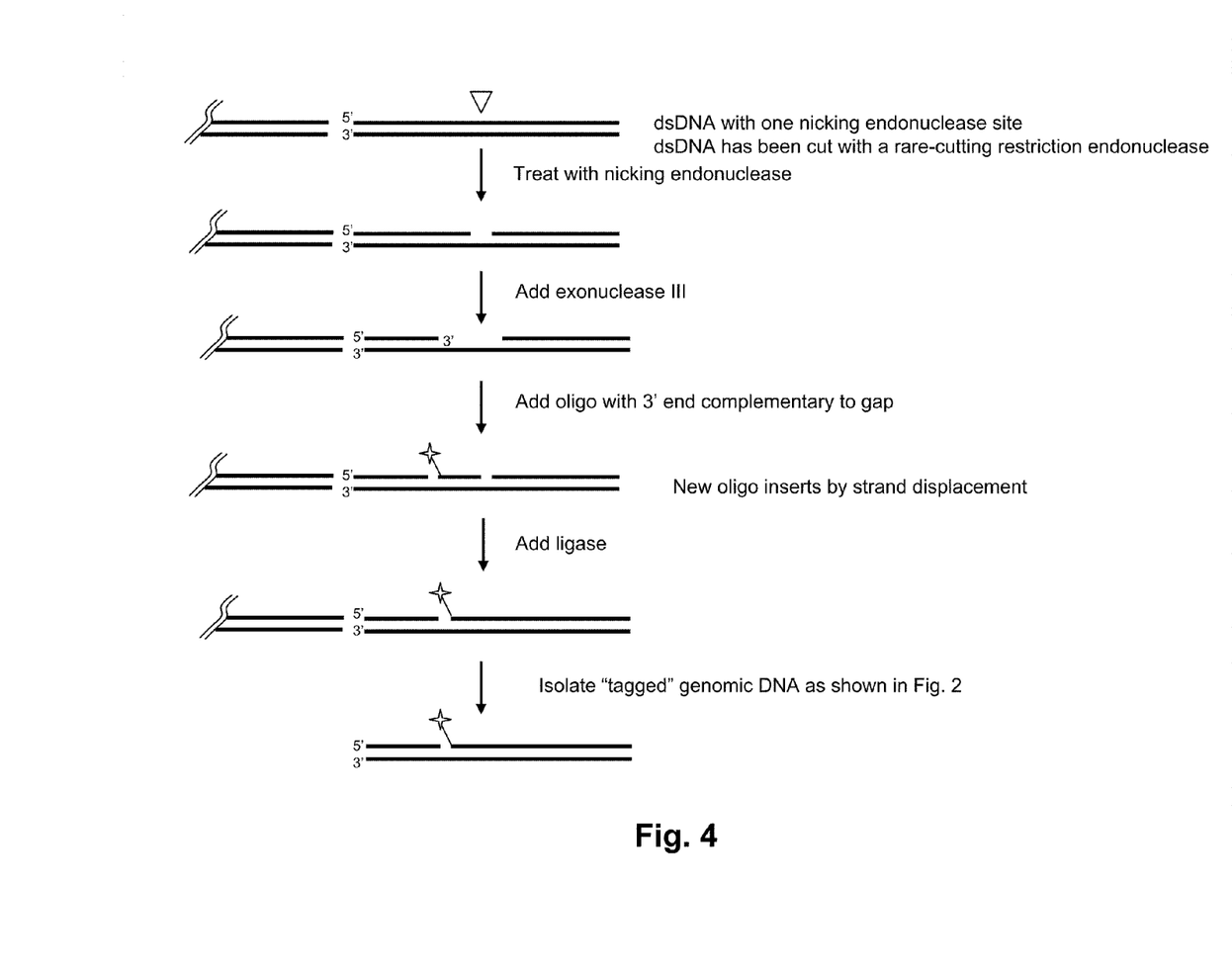
FIG. 4 schematically illustrates a second embodiment of a genome partitioning method described in greater detail below.

The test genome may be isolated from any organism. The organism may be a prokaryote or a eukaryote. In certain cases, the organism may be a plant, e.g., *Arabidopsis* or maize, or an animal, including reptiles, mammals, birds, fish, and amphibians. In some cases, the test genome may be human or rodent, such as a mouse or a rat. Methods of preparing genomic DNA for analysis is routine and known in the art, such as those described by Ausubel, F. M. et al., (*Short protocols in molecular biology*, 3rd ed., 1995, John Wiley & Sons, Inc., New York) and Sambrook, J. et al. (*Molecular cloning: A laboratory manual*, $2^{nd}$ ed., 1989, Cold Spring Harbor Laboratory Press, Cold Spring Harbor, N.Y.). In certain cases, the sample digested by the nicking endonuclease may contain unamplified or amplified genomic DNA that may be undigested or digested with a restriction endonuclease (i.e., an enzyme that cleaves both strands to yield double-stranded fragments, where the restriction enzyme may have a four, five, six, seven, eight, nine, ten or greater than ten base pair recognition site) or fragmented by other means (e.g., sonication). FIGS. 1 and 4 illustrate an embodiment in which the genome is digested with a restriction enzyme prior to digestion with the nicking enzyme.

Since genomic isolation methods, nicking enzyme recognition sites and the nucleotide sequences of many organisms (including many bacteria, fungi, plants and animals, e.g., mammals such as human, primates, and rodents such as mouse and rat) are known, nicking a test genome at a site that is proximal to a region of interest is within the skill of one of skilled in the art.

After the genome is nicked to produce a nicked double-stranded genomic region that contains a nick site between two nucleotides (between a "first" nucleotide and a "second" nucleotide), the nicked double-stranded genomic region is hybridized with an affinity tagged oligonucleotide that is complementary to the nucleotide sequence that flanks the nick site to produce a duplex in which a terminal nucleotide of the oligonucleotide (i.e., a nucleotide at either the 3' or the 5' end of the oligonucleotide) lies immediately adjacent to the first or second nucleotide of the nick site. The nucleotide sequence immediately flanking the nick site is effectively replaced with an oligonucleotide. As will be described in greater detail below, the replacement of the nucleotide sequence that flanks the nick site with an oligonucleotide can be done using a number of different protocols, including by stand displacement protocol (shown in FIGS. 1, 5, and 6) or by an exonuclease-based protocol (shown in FIG. 4), although other methods may be used.

Figure 5:
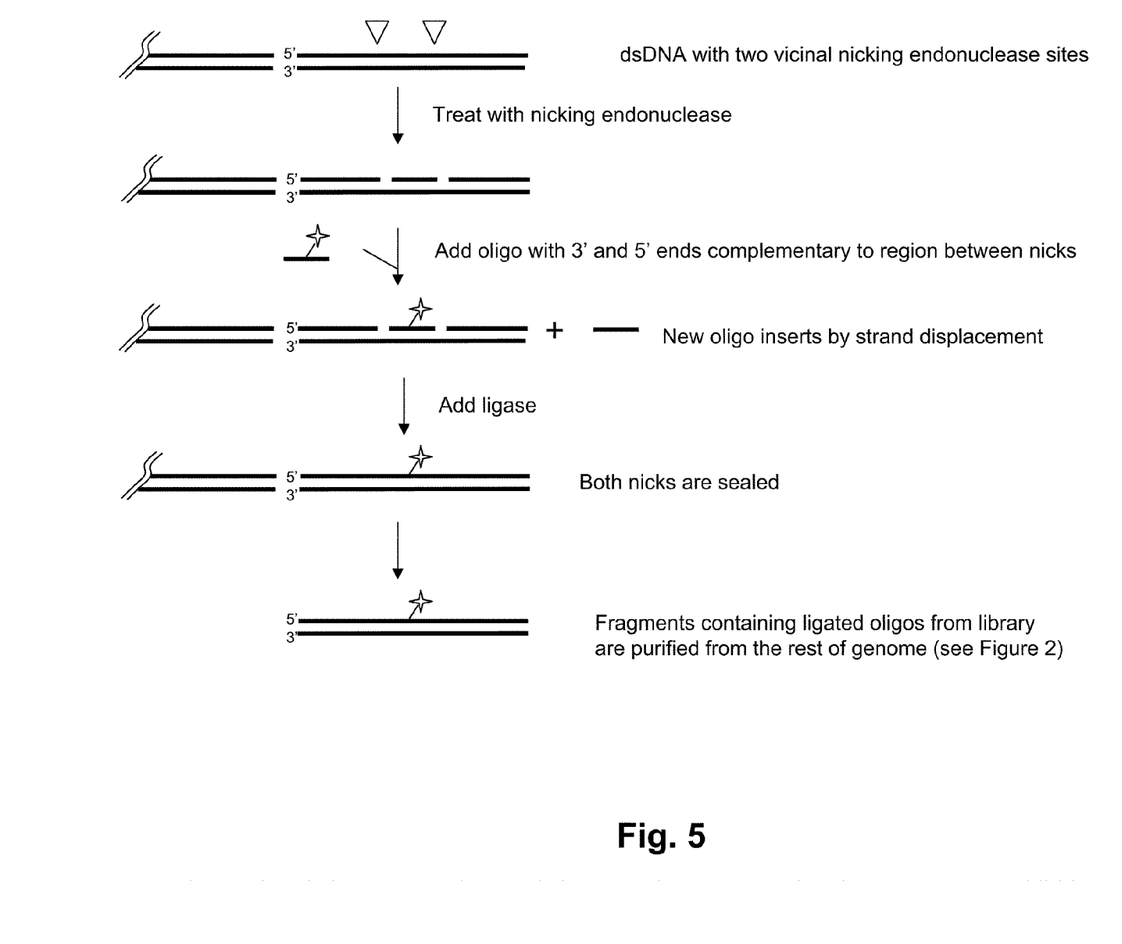
FIG. 5 schematically illustrates another embodiment of a genome partitioning method described in greater detail below.
Figure 6:
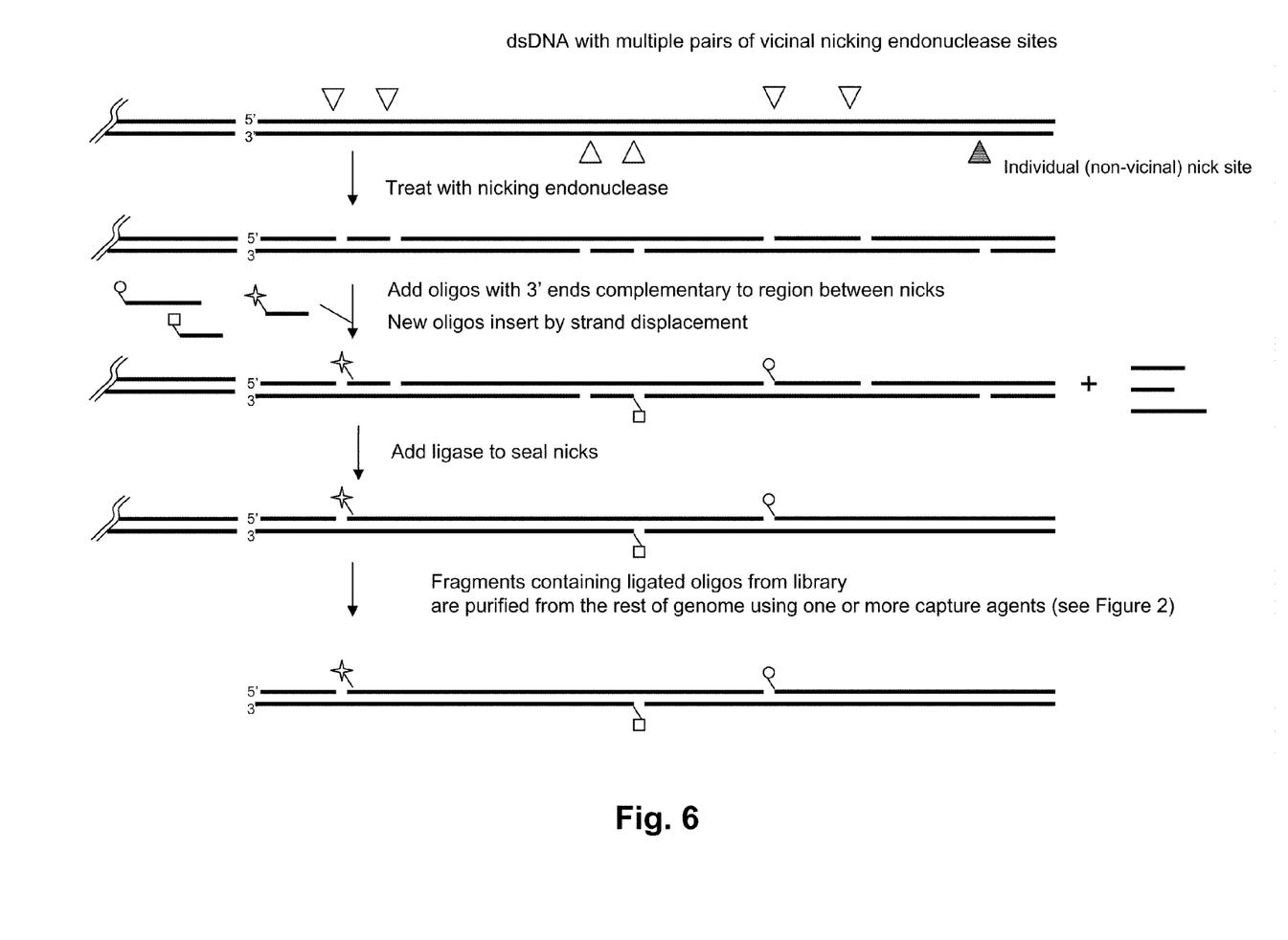
FIG. 6 schematically illustrates another embodiment of a genome partitioning method using multiple oligonucleotides.

In the strand displacement protocol (as illustrated in FIGS. 1, 5, and 6), the test genome may be nicked at two neighboring sites (i.e., "vicinal" sites) on the same strand that are 15 to 500 nucleotides (e.g., in the range of 18 to 200 nucleotides, in the range of greater than 25 to 200 nucleotides or in the range of greater than 50 to 200 nucleotides) apart, and the nicked region may be contacted with a molar excess (e.g., a 5- to 1,000-fold, e.g., 10- to 100-fold molar excess) of oligonucleotide under conditions suitable for strand displacement (i.e., displacement of the single-stranded nucleic acid between the nick sites by the oligonucleotide). Conditions for strand displacement are known (see, e.g., Walker, PCR Methods Appl. 1993 3:1-6; Kuhn Nucleic Acids Res. 2008 36: e40; and Coma et al Oligonucleotides 2005 15:269-83, among many others) and generally include non-stringent hybridization conditions (e.g., incubation if a double-stranded target and an oligonucleotide in a moderate temperature in the range of 30° C. to 70° C.). In certain embodiments of this method, the oligonucleotide may have a nucleotide sequence that is identical to the fragment that is being displaced. For example, if the fragment between the nick sites is 150 nucleotides in length, then the oligonucleotide may be 150 nucleotides in length. In other embodiments, the oligonucleotides may be longer or shorter than the replaced fragment by e.g., up to 5%, up to 10% or up to 20% or more, for example.

In the alternative exonuclease-based method (illustrated in FIG. 4) the nicked double-stranded genomic region is contacted with an exonuclease, e.g., exonuclease III, under conditions in which the exonuclease is active in order to progressively remove the nucleotides that flank the nick site in the nicked double-stranded genomic region prior to hybridization of the oligonucleotide. Since this reaction is progressive and occurs at a defined rate (i.e., it is known how many nucleotides are removed by the exonuclease per minute), the reaction can be initiated and stopped when a sufficient number of nucleotides (e.g., in the range of 50 to 2,000, e.g., 200 to 1,000) have been removed. Since the processivity of many exonucleases is known, this time is readily calculable. This embodiment of the method does not require that the number of nucleotides removed is the same as or greater then the number of complementary nucleotides in the oligonucleotide. Rather, a sufficient number of nucleotides should be removed to allow the oligonucleotide to anneal to the exposed strand to form a duplex. In this embodiment therefore, the nucleotide at the 3' end of the oligonucleotide may lie immediately adjacent to 5' nucleotide of the nick site, and the 5' end of the oligonucleotide may or may not be annealed to the genomic region. Once the nicked double-stranded genomic region has been digested with an exonuclease for a specified period of time, the exonuclease may be inactivated, and the exonuclease-treated sample may be contacted with the oligonucleotide under suitable hybridization conditions to produce a duplex.

As noted above, the oligonucleotide contains an affinity tag, i.e., a moiety that specifically binds to a capture agent that can be used to separate any molecules containing the affinity tag from molecules that do contain the affinity tag. The affinity tag may be joined to the nucleotides of the oligonucleotide at any position (e.g., at the 3'end, the 5' end or at a position in the middle of the oligonucleotide). In certain cases, the affinity tag may be biotin (the capture agent for which is, e.g., streptavidin) or a so-called "bar code" nucleotide sequence that is unique to the oligonucleotide that distinguishes it from other nucleic acids. The capture agent for a barcode sequence is a complementary nucleotide sequence. An example of an oligonucleotide containing a barcode sequence and a capture sequence for the barcode is provided below.

Figures 2A, 2C:
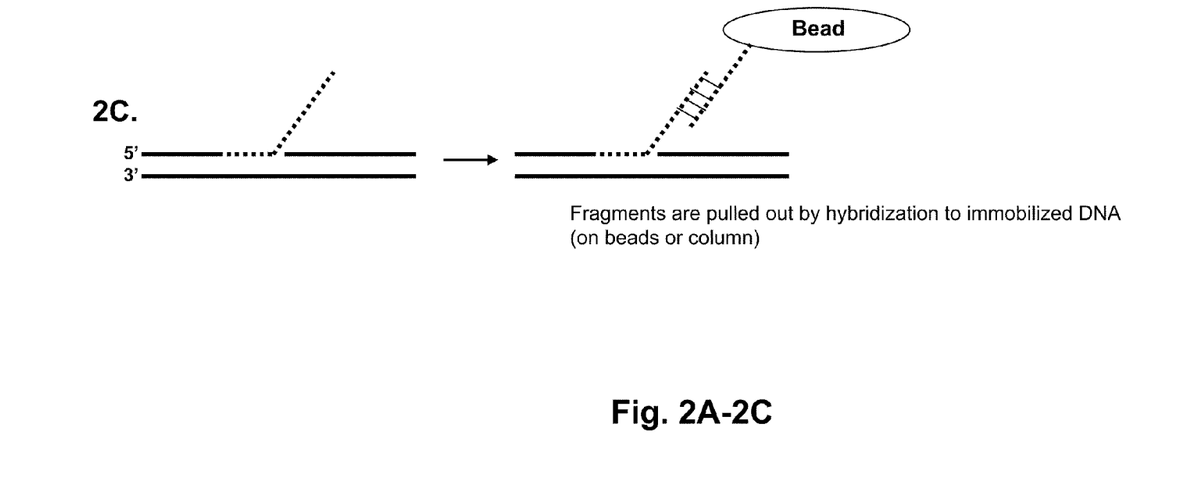

The affinity tag may be linked to the oligonucleotide at any position, including, but not limited to, the 5' end, the 3' end or any position in the interior of the oligonucleotide, e.g., in the middle of the oligonucleotide. As will be described in greater detail below, the affinity tag may be cleavably linked to the oligonucleotides such that it can be cleaved from the nucleotide after the separation step. In one exemplary embodiment, the affinity tag may be part of a nucleotide sequence that is added to the end of the oligonucleotide to facilitate cleavage of the affinity tag from the oligonucleotides using a nuclease. Various embodiments of this method are illustrated in FIGS. 2A-2C.

In certain embodiments more than one oligonucleotide may be ligated to a genomic region. For example, if a duplex region of the genome is targeted, one or more oligonucleotides may be designed to hybridize to nick sites occurring on each strand of the duplex (FIG. 6).

Since the nucleotide sequences of many genomes are known, the design and use of an oligonucleotide employed in the subject method should be well within the skill of one of skill in the art. In one embodiment, a region of a genome may be chosen and the nick sites for various nicking endonucleases may be mapped onto the region in order to identify one or more nicking endonucleases that nick near or in the chosen region. In particular embodiments, a single nicking endonuclease that creates vicinal nicks near or in the chosen region (e.g., in the strand-displacement protocol) may be chosen. In other embodiments, if a plurality of nicking endonucleases are employed (e.g., in the strand-displacement protocol) different nicking endonucleases that nick at vicinal sites may be chosen. In the graph shown in FIG. 7, the nick sites were mapped in a 90 kb region encompassing the HER2 gene. A variety of vicinal nick sites created by nicking endonucleases were identified. As noted above, an oligonucleotide used in the method may be the same length as the distance between to vicinal nick sites (e.g., from 25-200 nts in length). Once the nick sites for nicking endonucleases have been mapped to a genomic region, the nucleotide sequence of such oligonucleotides would be apparent. As would be readily apparent, if the affinity tag is at one end of the oligonucleotide, it should not block the end of the oligonucleotide that is to be ligated to the genomic nucleic acid. As such, if the 5' end of the oligonucleotides is to be ligated to the adjacent nucleotide (which would be at the 3' end of a genomic strand), then the affinity tag should not block the ligation. In these embodiments, the affinity tag may be at the 3'end or interior of the oligonucleotides, and the oligonucleotides should contain a 5' phosphate to enable ligation. Likewise, if the 3' end of the oligonucleotide is to be ligated to the adjacent nucleotide (which would be at the 5' end of a genomic strand), then the affinity tag should not block the ligation. In these embodiments, the affinity tag may be at the 5'end or interior of the oligonucleotides. In certain embodiments and as mentioned above, an oligonucleotide may contain other features, e.g., a cleavable linker or a hairpin region (FIG. 2B) that can used to cleave the affinity tag from the oligonucleotides. In a particular embodiment, the oligonucleotide may contain a promoter, e.g., a DNA polymerase or an RNA polymerase promoter for T7 or T3 polymerase, so that the separated nucleic acid can be amplified prior to use.

In particular embodiments, a subject oligonucleotide may contain so-called unstructured nucleic acid nucleotides (UNAs), which nucleotides are known and may be synthesized synthetically (Kutyavin et al., Nucl. Acids Res. (2002) 30:4952-4959). UNA oligonucleotides may have a reduced tendency towards self-hybridization in comparison to unmodified oligonucleotides, and thus UNA oligonucleotides may be more effective than unmodified oligonucleotides in the strand displacement reaction. In certain embodiments, oligonucleotides comprising so-called locked nucleic acids (LNAs) may be used (Vester and Wengel, Biochemistry (2004) 43:13233-41). The use of LNA oligonucleotides may promote stronger binding of incoming oligonucleotide strand to the genomic DNA compared with the native strand. This would favor the strand displacement reaction, and drive it forward. Alternatively, proteins such as RecA, Rad51, or certain chemical conditions can promote strand exchange. Such enzymes and/or conditions could be employed to enhance the strand displacement reaction. In embodiments, oligonucleotide modifications such as LNA or UNA modifications may be used alone or in combination, or in combination with enzymes or conditions favoring the strand displacement reaction. In one embodiment, an oligonucleotide may amplified prior to use by, e.g., linear (e.g., T7 polymerase-based) methods or by PCR, for example.

After the nicked double-stranded region has been hybridized with an oligonucleotide to produce a duplex in which a terminal nucleotide of the oligonucleotide lies immediately adjacent to said a nucleotide of the nick site, the duplex is contacted with a ligase under conditions suitable for the enzyme to ligate the terminal nucleotide of the oligonucleotide to the remaining nucleotide of the nick site to produce a ligation product. The affinity tagged oligonucleotides thereby becomes covalently linked to the strand of the genomic region that lies adjacent to the ligated nick site, and that region (including double- and single-stranded forms of the region) can be separated from the remainder of the test genome (i.e., the remainder of the test genome that is unligated to the oligonucleotides) using the affinity tag. In general terms, this separation step may include contacting the ligation products with a capture agent for the affinity tag under conditions suitable for specific binding of the affinity tag to its capture agent. Such conditions for, e.g., biotin/streptavidin and barcode tags, are known. The capture agent may be immobilized or immobilizable on a support, e.g., a bead (FIG. 2C) or on a glass slide in the form of an array, and, after the ligation products are contacted with the capture agent, the resultant composition may be washed to remove unligated products from the solid support. The separation step thereby produces two fractions, one containing the selected genomic region (that is ligated to the affinity tagged oligonucleotides) and the other that does not contain the selected genomic region. As such, the method may be employed to isolate any region or regions of a genome.

In certain embodiments and as mentioned above, the selected genomic region may be isolated in single-stranded or double-stranded form. As such, in addition to the steps described above, the method may or may not further include denaturing the two strands of the selected genomic region after the oligonucleotide is ligated to the region. This denaturation step may occur at any point in the method after ligation, e.g., before or after the separation step described above.

Also as noted above, in certain embodiments, the affinity tag may be cleaved from the separated products by any suitable method. Since a variety of cleavable linkers (e.g., photocleavable or chemically-cleavable) linkers could be used to link the affinity tag to the oligonucleotide or the oligonucleotide could be designed to contain a hairpin region that contains a recognition site for a restriction enzyme (e.g., a enzyme that recognizes at least a six-base pair cleavage site or at least an eight base pair cleavage site; FIG. 2B), for example, this cleavage step can be readily performed. In one embodiment, the capture agent of the affinity tag may be immobilized to a support, the ligation products may be contacted with the support under conditions suitable for binding of the affinity tag to the capture agent, thereby separating the ligated products from the unligated products and immobilizing the ligation products on the support, and then cleaving the oligonucleotide from the affinity tag, thereby releasing the ligation products into the soluble phase where they can be removed for further analysis.

In particular embodiments, the method may further include cleaving, e.g., using a restriction endonuclease (i.e., an enzyme that cleaves both strands of a double-stranded DNA at the enzyme's recognition sequence; a restriction enzyme) prior to or after any of the steps. For example, the genome sample may be digested prior to nicking, between nicking and hybridization of the oligonucleotide, between hybridization of the oligonucleotide and ligation, between ligation and separation, or after separation. In particular embodiments, this restriction endonuclease (which may in certain embodiments have a recognition site that is at least 6 base pairs, e.g., at least 7, at least 8, at least 9 or at least 10 base pairs in length) may be chosen so that it cleaves at a particular distance from the nick site to provide a separated product of defined length. Depending on the length desired and the availability of nicking and restriction endonucleases, the separated product may be a length in the range of 500 bases to 100,000 kb, e.g., 1 kb to 50 kb, 2 kb to 10 kb or 10 kb to 100 kb in length. As such, in certain embodiments, the method may be employed to separate a single or double-stranded product of a defined length, from a selected region of a genome. In alternative embodiments, the nucleic acid may be cleaved using an alternative method, e.g., by a physical (sonication) or chemical method.

Figure 3:
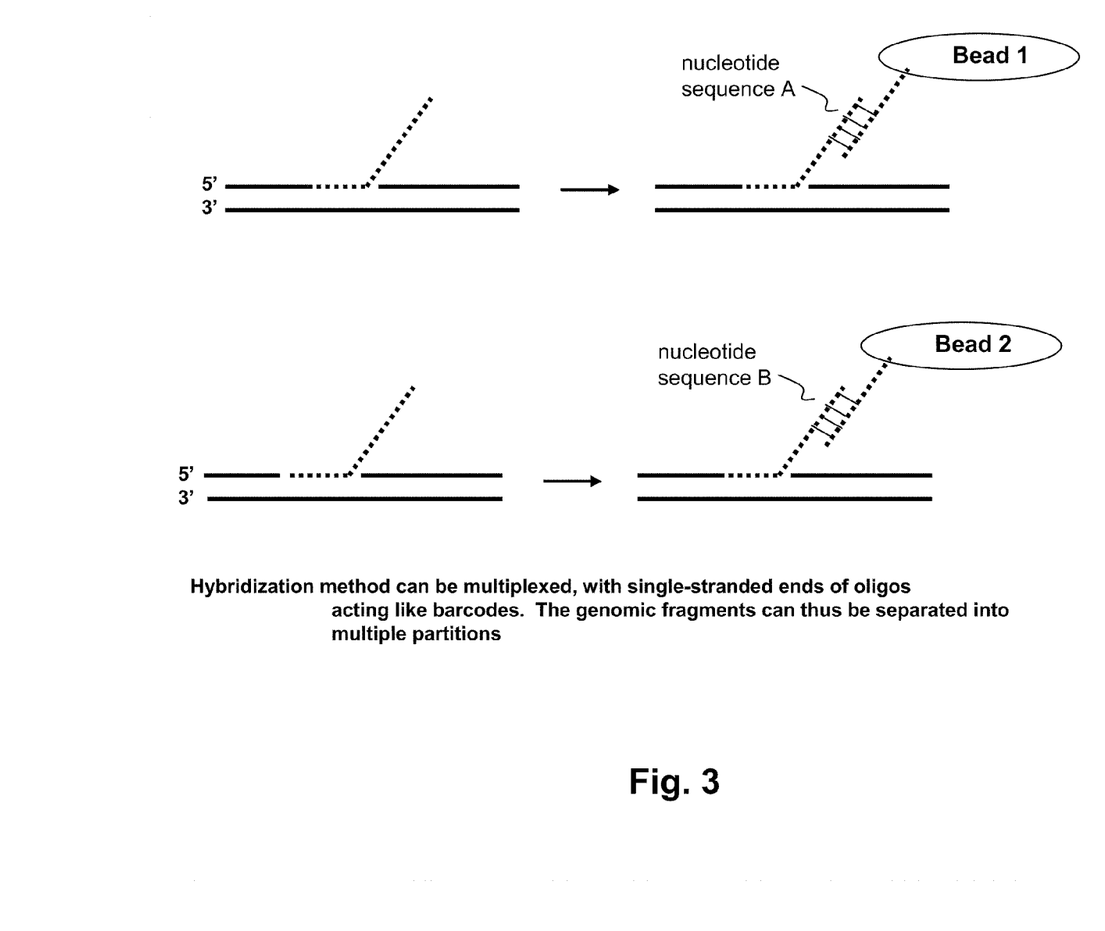
FIG. 3 schematically illustrates an exemplary method for isolating a genomic region that employs oligonucleotide barcodes.

The method described above may be done using a single oligonucleotide or a plurality (i.e., a mixture of at least 2, at least 5, at least 10, at least 50, at least 100, at least 500 or at least 1,000, up to 10,000 or 100,000 or more oligonucleotides) of different oligonucleotides in a multiplex reaction that can be used to isolate a plurality of different genomic regions. In certain embodiments, if a plurality of different oligonucleotides are used, they may all contain the same affinity tag. In certain embodiments, if a plurality of different oligonucleotides are used, more than one oligonucleotide may bind to the same genomic region (FIG. 6). In these embodiments, the genomic region may be isolated using a plurality of affinity tags that bind to a single capture agent, or a plurality of affinity tags which bind to a plurality of capture reagents. In yet other embodiments, if a plurality of different oligonucleotides are used to bind to different genomic regions, they may each contain a different affinity tag such that one oligonucleotide in the plurality can be separated from the other oligonucleotides in the plurality using the affinity tag. This may be done using nucleotide barcodes, as discussed above, although other techniques are available. In these embodiments, the ligation products may be separated from the products that are not ligated using a single capture agent (e.g., biotin), or a plurality of different capture agents that bind to corresponding affinity tags. In this latter embodiment, the capture agents may be affixed to a spatially or optically addressable array (e.g., in a spatially-addressable planar array or optically-addressable beads) of where one capture agent is affixed to one address of the array (see FIG. 3). The ligation products may be contacted with the addressable array, and the different ligation products will become associated with a particular address of the array. The captured ligation products may then be analyzed en mass (by releasing them from the entire array), or individually, by releasing them from a single address at a time.

As would be readily apparent, if the affinity tag is attached to the interior of the oligonucleotide and the nucleotide sequence of the oligonucleotide is identical to and the same length as the sequence of nucleotides between two nick sites, the oligonucleotide may be ligated to nucleic acid on both sides of the oligonucleotide (FIG. 5). As such, in certain embodiments, the subject method may be employed to both flanking regions of the oligonucleotide.

Compositions

In addition to the method described above, a number of compositions are also provided. In certain embodiments, the composition may contain a population of at least two different oligonucleotides, wherein each of said oligonucleotides contains an affinity tag and is complementary to a nucleotide sequence that is immediately adjacent to a nick site of a sequence-specific nicking endonuclease in a mammalian genome. In certain embodiments, the population of oligonucleotides may be a mixture of oligonucleotides that may in the form of a dried pellet or an aqueous solution. In particular embodiments, the different oligonucleotides are attached to a solid support in the form of an array.

In certain embodiments, the oligonucleotides are synthesized on a solid support in an array, where the oligonucleotides are grown in situ. Oligonucleotide arrays can be fabricated using any means, including drop deposition from pulse jets or from fluid-filled tips, etc, or using photolithographic means. Polynucleotide precursor units (such as nucleotide monomers), in the case of in situ fabrication can be deposited. Oligonucleotides synthesized on a solid support may then be cleaved off to generate the population of oligonucleotides. Such methods are described in detail in, for example U.S. Pat. Nos. 7,385,050, 6,222,030, 6,323,043, and US Pat Pub No. 2002/0058802, etc., the disclosures of which are incorporated herein by reference. The oligonucleotides may be tethered to a solid support via a cleavable linker, and cleaved from the support before use.

In particular embodiments, the oligonucleotides may be complementary to 25 to 200 contiguous nucleotides between two adjacent nick sites in a genome, where the nick sites are 25 to 500 nucleotides apart. In certain embodiments, the oligonucleotides may be the same length as the distance between the two nick sites.

Kits

Also provided by the subject invention are kits for practicing the subject method, as described above. The subject kit contains a set of at least 2, at least 10, at least 1,000, or at least 10,000 or more oligonucleotides, as described above, as well as, for example, a sequence-specific nicking endonuclease, and a ligase enzyme. In particular embodiments, the kit may further contain an exonuclease (for use in the exonuclease protocol discussed above) and/or a capture agent (e.g., streptavidin or a complementary set of oligonucleotides) for capturing the ligation products described above. In a particular embodiment, the kit may contain an array of different capture agents (e.g., an array of oligonucleotides that are complementary to the barcodes used in the assay).

In additional embodiments, the kit may further contain information on the nick sites for a plurality of different nicking endonucleases. This information may be in electronic form, and may be used to identify suitable nicking endonucleases for analyzing a chosen genomic region.

In addition to the instructions, the kits may also include one or more control genomes and or oligonucleotides for use in testing the kit.

In addition to above-mentioned components, the subject kit may further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The various components of the kit may be in separate containers, where the containers may contained within a single housing, e.g., a box.

Utility

The above-described method may be used to partition a genome, i.e., to isolate one or more chosen regions of a genome (which may be single-stranded or double-stranded) from other regions of the genome. The genomic regions partitioned by the subject method may be arbitrarily chosen or, in some embodiments may have a common function, structure or expression. While the above-described method is not so limited, the method may be employed to isolate promoters, terminators, exons, introns, entire genes, homologous genes, sets of gene sequences that are linked by function, expression or sequence, regions containing insertion, deletion or translocation breakpoints or SNP-containing regions, for example. Alternatively, the method could be used to reduce the sequence complexity of a genome prior to analysis, or to enrich for genomic regions with fewer repeated sequences.

In certain embodiments the method may be used to enrich for one or more ligation products (i.e., one or more regions of a genome), where the resultant sample is at least 50% free, e.g., at least 80% free, at least 90% free, at least 95% free, at least 99% free of the remainder of the genome, where at least at least 10%, at least 30%, at least 50%, at least 80% or at least 90% or at least 95% of the chosen genomic regions are partitioned into the isolated products and the remainder is partitioned into the unligated products. As noted above, in addition to isolating a single genomic region, the method (when used with a plurality of different oligonucleotides in a multiplex reaction) can be used to enrich for a plurality (i.e., at least 2, e.g., at least 5, at least 10, at least 50, at least 100, at least 500, at least 1,000, at least 5,000, at least 10,000 up to 50,000 or more different genomic regions.

In particular embodiments, the products of the method may be amplified before analysis. In other embodiments, the products of the method may be analyzed in an unmodified form, i.e., without amplification.

As noted above, the method may be employed to isolate a region of interest from genome. The isolated region may be analyzed by any analysis method including, but not limited to, DNA sequencing (using Sanger, pyrosequencing or the sequencing systems of Roche/454, Helicos, Illumina/Solexa, and ABI (SOLID)), a polymerase chain reaction assay, a hybridization assay, a hybridization assay employing a probe complementary to a mutation, a microarray assay, a bead array assay, a primer extension assay, an enzyme mismatch cleavage assay, a branched hybridization assay, a NASBA assay, a molecular beacon assay, a cycling probe assay, a ligase chain reaction assay, an invasive cleavage structure assay, an ARMS assay, or a sandwich hybridization assay, for example. Some products (e.g., single-stranded products) produced by the method may be sequenced, analyzed for the presence of SNPs or other differences relative to a reference sequence. As would be clear to one skilled in the art, the proposed method may be useful in several fields of genetic analysis, by allowing the artisan to focus his or her analysis on a genomic region of interest.

The subject method finds particular use in SNP haplotyping of a chromosomal region that contains two or more SNPs, for enriching for DNA sequences for paired-end sequencing methods, for generating target fragments for long-read sequences, isolating inversion, deletion, and translocation breakpoints, for sequencing entire gene regions (exons and introns) to uncover mutations causing aberrant splicing or regulation, and for the production of long probes for chromosome imaging, e.g., Bionanomatrix, optical mapping, or fiber-FISH-based methods.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

EXAMPLE 1

Figure 7:
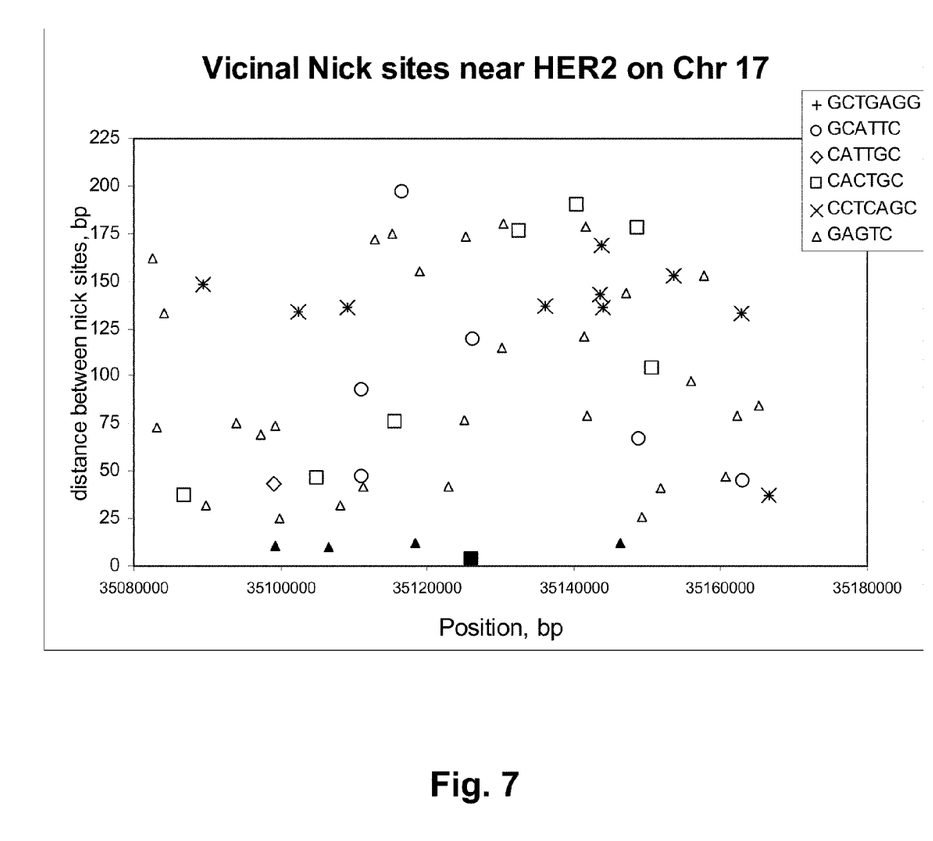
FIG. 7 is a graph showing the distribution of vicinal nicking endonuclease nick sites in a chromosomal region.

In an in silico test, the frequency of vicinal nick sites that could be created by a single nicking endonuclease in a genomic region was determined. In this test, vicinal nick sites were defined as nick sequences on the same strand within 200 bp, whereas break sequences were nicks created on opposite strands within 25 bp. Six nicking endonuclease sequences were mapped in four regions of the human genome ranging from 73 to 96 kilobases. A total of 217 suitable vicinal nick sites were found distributed in the four target regions. FIG. 7 shows an example of the distribution of suitable vicinal nick sequences in a 90 kb region of the genome encompassing the HER2 gene. Although two of the tested sequences (GAGTC, triangles, and CACTGC, squares) may create breaks by creating closely-spaced nicks on opposite strands (shown as filled symbols), the other four nicking endonucleases create a variety of vicinal nick sequences suitable for targeting with the proposed method (shown as open symbols). Notably, in this test, the vicinal nicks are created with spacings from 25 to 200 bp apart, so even if the strand displacement reaction is most efficient with certain oligonucleotides (e.g., oligonucleotides over 100 bases in length), there are sufficient targets to ensure capture of the region. Furthermore, for any given enzyme, there are many more vicinal nick sequences than break sequences created. Finally, it is clear that a combination of nicking endonucleases may be used to create even more vicinal nick sequences. Such methods may be used to select the best nicking enzyme or combination of enzymes for a given region, in order to maximize the probability of capturing the target region while minimizing unnecessary DNA fragmentation.

EXAMPLE 2

Figure 8:
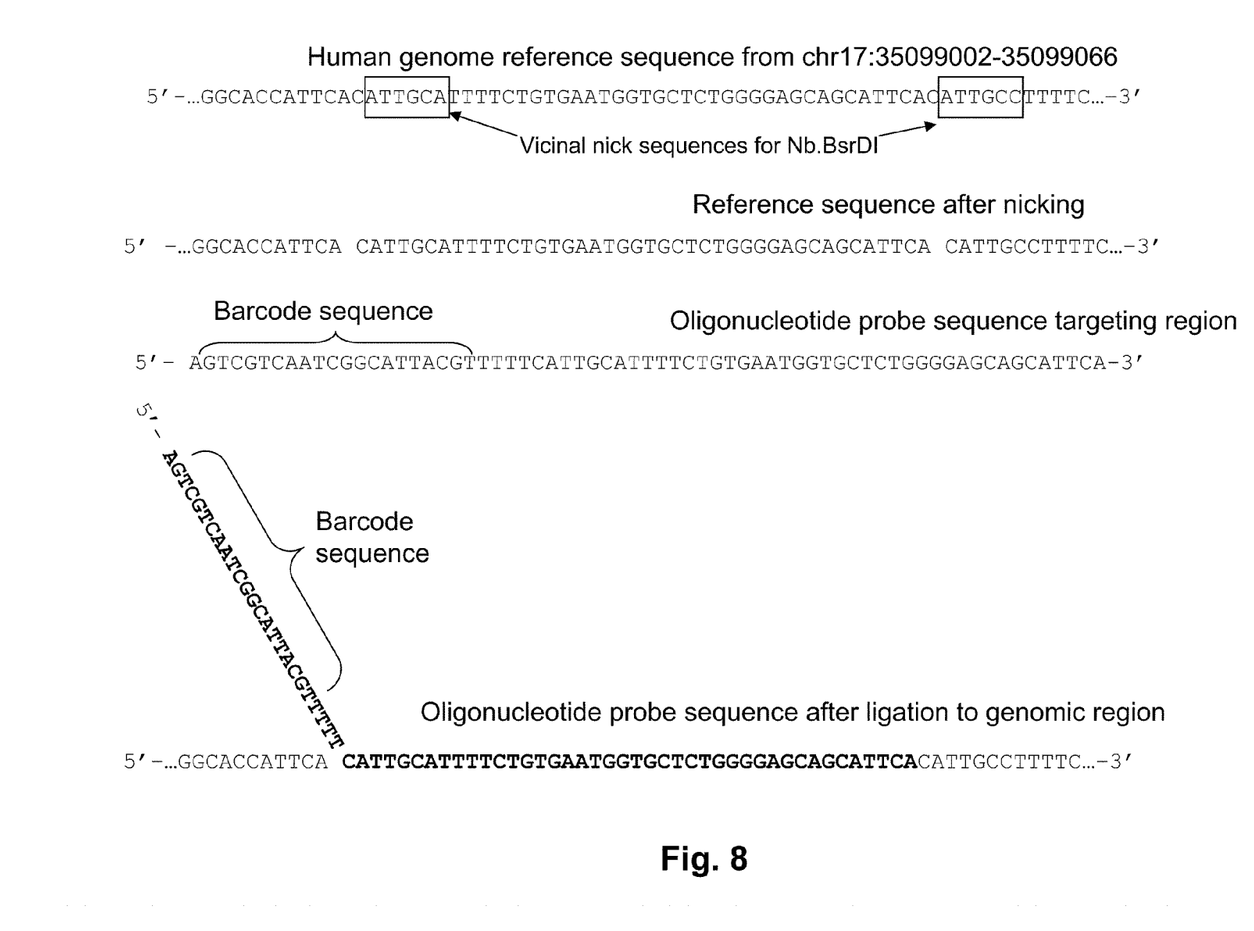
FIG. 8 schematically illustrates aspects of the method for a particular sequence. SEQ ID NOS:1-6.

FIG. 8 shows a detailed embodiment of the method. Reference sequence from the human genome is shown (only the + strand of the duplex is shown for clarity). The enzyme Nb.BsrDI creates vicinal nicks 42 nucleotides apart on the same strand. This pair of vicinal nick sequences is also indicated by a diamond symbol in FIG. 7. An oligonucleotide with SEQ ID NO. 1 can replace the genomic sequence between the nicks by strand displacement, and can be attached to the genomic region by ligation. The oligo with SEQ ID NO. 1 comprises a 20nt "barcode" sequence at the 5' end, followed by a short linker sequence, and the 3' end is identical to the genomic sequence to be replaced. The reverse complement of the barcode sequence, SEQ ID NO. 2, can be fixed to a solid support and used to isolate the genomic region.

Depending on the degree of genomic DNA fragmentation and the isolation conditions, multiple kilobases of the HER2 region could be partitioned from the remainder of the genome.

SEQ ID NO. 3 is listed as an example of a oligonucleotide sequence comprising a biotin affinity tag, which is designed to target vicinal nicks in the HER2 region (chr17:35163121-35163165) created by the nicking endonuclease Nb.BsmI.

Nicking Endonuclease Reaction:

5 micrograms of purified human genomic DNA 40 units of Nb.BsrDI enzyme (New England Biolabs, Ipswich, Mass., USA)

1× NEB buffer #2 (New England Biolabs, Ipswich, Mass., USA)

A 50 microliter reaction is incubated for 4 hours at 65 degrees centigrade before a 20 minute incubation at 80 degrees centigrade to inactivate the enzyme.

Strand Displacement Reaction:

The nicked genomic DNA sample is incubated with a 100-fold molar excess of probe oligonucleotide (e.g., an oligonucleotide with SEQ ID NO. 3) at 50 degrees centigrade in a buffer containing 10 mM Tris-HCl (pH 7.4), 0.1 mM EDTA to allow strand invasion. After a 48 hour incubation, the sample is cooled to 16 degrees centigrade at a rate of 0.1 degree per minute.

Ligation Reaction:

Ligation reactions are performed by adding 10× ligation reaction buffer (New England Biolabs, Ipswich, Mass., USA) and 10 units of T4 DNA ligase (New England Biolabs, Ipswich, Mass., USA) and incubating at 16 degrees centigrade for 2 hours. Ligation reactions are terminated by addition of EDTA to 20 mM.\

Capture of Genomic Region:

After ligation of the biotinylated oligonucleotide to the genomic region, DNA comprising the genomic region is isolated using Dynabeads® M-270 streptavidin (Invitrogen Corp, Carlsbad, Calif., USA) according to the manufacturer's instructions. The genomic region could be released from the streptavidin beads by treatment with a ssDNA nuclease, such as Mung Bean Nuclease (New England Biolabs, Ipswich, Mass., USA).

The size of the actual genomic region that is isolated will depend on the degree of DNA fragmentation in the original DNA sample. The skilled artisan will understand that certain methods such as minimal pipetting of the sample may reduce the degree of fragmentation, and should allow the isolation of multi-kilobase genomic regions. Treatment of the genomic DNA with a restriction endonuclease (e.g., a rare cutting endonuclease such as NotI) would allow the isolation of genomic regions of a defined size. For large genomic regions (e.g., >50 kilobases), genomic region of interest may be targeted with a plurality of oligonucleotides to ensure efficient capture of a genomic region.

SEQ ID NO. 5: Strand invasion oligonucleotide for HER2 region with a 5' barcode sequence

5'-AGTCGTCAATCGGCATTACGTTTTTCATTGCATTTTCTGTGAATGGT

GCTCTGGGGAGCAGCATTCA-3'

SEQ ID NO. 7: Capture sequence for SEQ ID NO. 1

5'-CGTAATGCCGATTGACGACT-3'

SEQ ID NO. 8: Strand invasion oligonucleotide for HER2 region with a 5' biotin affinity tag.

5' [Biotin] - TTTTTTTTTCATTCACCTGCCCAACTCCCATGCCC

TGAGTCCTGTCCTCCAGGG - 3'

---

What is claimed is:

1. A method for partitioning a genome comprising:
   a) nicking a region of said genome using a sequence-specific nicking endonuclease to produce a nicked double-stranded genomic region comprising a first nick site between a first nucleotide and a second nucleotide;
   b) hybridizing said nicked double-stranded genomic region with an oligonucleotide comprising:
      i. an affinity tag; and
      ii. a nucleotide sequence that is complementary to the nucleotide sequence that is immediately adjacent to said first nick site;

to produce a duplex in which a terminal nucleotide of said oligonucleotide lies immediately adjacent to said first nucleotide;

c) ligating said terminal nucleotide of said oligonucleotide to said first nucleotide to produce a ligation product; and d) separating said ligation product from unligated products using said affinity tag, thereby partitioning said genome.

2. The method of claim 1, wherein said hybridizing is done by removing said nucleotide sequence using an exonuclease to provide a single-stranded region, and then hybridizing said oligonucleotide to said single-stranded region.

3. The method of claim 1, wherein said hybridizing is done using a strand displacement protocol that comprises:
   i. nicking said double-stranded genomic region at a second nick site; and
   ii. displacing the nucleotide sequence between said first nick site and said second site using said oligonucleotide.

4. The method of claim 3, wherein said first nick site and said second nick site are separated by at least 25 nucleotides and less than 200 nucleotides.

5. The method of claim 1, wherein said hybridizing is done using a molar excess of said oligonucleotide.

6. The method of claim 1, wherein said nicking comprises contacting said genome with a plurality of different nicking endonucleases.

7. The method of claim 1, wherein said oligonucleotide comprises unstructured nucleic acid.

8. The method of claim 1, wherein said method employs a population of different oligonucleotides.

9. The method of claim 8, wherein each oligonucleotide of said population comprises a molecular barcode that allows separation of said oligonucleotide from other oligonucleotides of said population.

10. The method of claim 1, wherein said genome is a mammalian genome.

11. The method of claim 1, wherein said separating includes separating a double-stranded DNA molecule comprising said oligonucleotide from unligated products.

12. The method of claim 1, wherein said separating includes separating a single-stranded DNA molecule comprising said oligonucleotide from unligated products.

13. The method of claim 1, wherein said genome is an unamplified genome.

14. The method of claim 1, further comprising digesting said genome prior to said separating step d).

15. The method of claim 1, wherein one genome fragment is ligated to a plurality of oligonucleotides.

16. A kit comprising:
   a) a population of at least two different oligonucleotides, wherein each of said oligonucleotides:
      i. comprises an affinity tag; and
      ii. is complementary to a nucleotide sequence that is immediately adjacent to a nick site of a sequence-specific nicking endonuclease in a mammalian genome;
   b) a sequence-specific nicking endonuclease; and
   c) a ligase enzyme.

17. The method of claim 3, wherein said ligating comprises ligating both the 3' and 5' terminal nucleotides of said oligonucleotide to the nucleic acid comprising said genomic region.

18. The method of claim 1, wherein the ligated products are greater than 5,000 nucleotides in length.

19. The kit of claim 16, wherein each of said oligonucleotides comprises a nucleotide sequence that is complementary to 15 to 500 consecutive nucleotides of said mammalian genome.

20. The kit of claim 16, wherein each of said oligonucleotides comprises a nucleotide sequence that is complementary to 18 to 200 consecutive nucleotides of said mammalian genome.

* * * * *

UNITED STATES PATENT AND TRADEMARK OFFICE
CERTIFICATE OF CORRECTION

PATENT NO. : 8,017,328 B2  
APPLICATION NO. : 12/276041  
DATED : September 13, 2011  
INVENTOR(S) : Robert A. Ach et al.

It is certified that error appears in the above-identified patent and that said Letters Patent is hereby corrected as shown below:

On the face page, in field (56), under "Other Publications", in column 2, line 1, delete "reconition" and insert -- recognition --, therefor.

On the face page, in field (56), under "Other Publications", in column 2, line 4, delete "restricrtion" and insert -- restriction --, therefor.

On the face page, in field (56), under "Other Publications", in column 2, line 14, delete "al.Genetic" and insert -- al. Genetic --, therefor.

In column 19, line 18, in Claim 3, after "second" insert -- nick --.

Signed and Sealed this  
Seventeenth Day of January, 2012

David J. Kappos  
*Director of the United States Patent and Trademark Office*

SEQUENCE LISTING

<160> NUMBER OF SEQ ID NOS: 8

<210> SEQ ID NO 1
<211> LENGTH: 65
<212> TYPE: DNA
<213> ORGANISM: Artificial Sequence
<220> FEATURE:
<223> OTHER INFORMATION: synthetic oligonucleotide

<400> SEQUENCE: 1
ggcaccattc acattgcatt ttctgtgaat ggtgctctgg ggagcagcat tcacattgcc    60
ttttc                                                                65

<210> SEQ ID NO 2
<211> LENGTH: 11
<212> TYPE: DNA
<213> ORGANISM: Artificial Sequence
<220> FEATURE:
<223> OTHER INFORMATION: synthetic oligonucleotide

<400> SEQUENCE: 2
ggcaccattc a                                                         11

<210> SEQ ID NO 3
<211> LENGTH: 42
<212> TYPE: DNA

```
<213> ORGANISM: Artificial Sequence
<220> FEATURE:
<223> OTHER INFORMATION: synthetic oligonucleotide

<400> SEQUENCE: 3
cattgcattt tctgtgaatg gtgctctggg gagcagcatt ca          42

<210> SEQ ID NO 4
<211> LENGTH: 12
<212> TYPE: DNA
<213> ORGANISM: Artificial Sequence
<220> FEATURE:
<223> OTHER INFORMATION: synthetic oligonucleotide

<400> SEQUENCE: 4
cattgccttt tc                                           12

<210> SEQ ID NO 5
<211> LENGTH: 67
<212> TYPE: DNA
<213> ORGANISM: Artificial Sequence
<220> FEATURE:
<223> OTHER INFORMATION: synthetic oligonucleotide

<400> SEQUENCE: 5
agtcgtcaat cggcattacg tttttcattg catttctgt gaatggtgct ctggggagca    60
gcattca                                                             67

<210> SEQ ID NO 6
<211> LENGTH: 79
<212> TYPE: DNA
<213> ORGANISM: Artificial Sequence
<220> FEATURE:
<223> OTHER INFORMATION: synthetic oligonucleotide

<400> SEQUENCE: 6
agtcgtcaat cggcattacg tttttcattg catttctgt gaatggtgct ctggggagca    60
gcattcacat tgccttttc                                                79

<210> SEQ ID NO 7
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 7
cgtaatgccg attgacgact                                   20

<210> SEQ ID NO 8
<211> LENGTH: 54
<212> TYPE: DNA
<213> ORGANISM: Artificial Sequence
<220> FEATURE:
<223> OTHER INFORMATION: synthetic oligonucleotide

<400> SEQUENCE: 8 ttttttttc attcacctgc ccaactccca tgccctgagt cctgtcctcc aggg          54
```